United States Patent
Aida et al.

(10) Patent No.: US 6,465,703 B1
(45) Date of Patent: Oct. 15, 2002

(54) PROCESS FOR THE CONTINUOUS PREPARATION OF TETRACYCLODODECENS

(75) Inventors: Fuyuki Aida, Kanagawa; Takashi Suzuki, Chiba; Yasuo Matsumura, Kanagawa, all of (JP)

(73) Assignee: Nippon Petrochemicals Co., Ltd., Tokyo (JP)

( * ) Notice: Subject to any disclaimer, the term of this patent is extended or adjusted under 35 U.S.C. 154(b) by 0 days.

(21) Appl. No.: 09/869,785
(22) PCT Filed: Nov. 10, 2000
(86) PCT No.: PCT/JP00/07933
§ 371 (c)(1),
(2), (4) Date: Jul. 5, 2001
(87) PCT Pub. No.: WO01/34541
PCT Pub. Date: May 17, 2001

(30) Foreign Application Priority Data

Nov. 10, 1999 (JP) ............................................. 11-319706

(51) Int. Cl.[7] ................................................ C07C 2/76
(52) U.S. Cl. ...................................... 585/360; 585/361
(58) Field of Search ................................. 585/360, 361, 585/350

(56) References Cited

U.S. PATENT DOCUMENTS 4,320,239 A  3/1982  Schneider ................... 585/360

FOREIGN PATENT DOCUMENTS

| JP | 3-128333 A1 | 5/1991 |
|---|---|---|
| JP | 6-9437 A1 | 1/1994 |
| JP | 10-287592 A1 | 10/1998 |
| WO | WO 00/01742 A1 | 1/2000 |

*Primary Examiner*—Thuan D. Dang
(74) *Attorney, Agent, or Firm*—Weingarten, Schurgin, Gagnebin & Lebovici LLP

(57) ABSTRACT

The present invention relates to a process for the preparation of tetracyclododecenes, which can be a raw material of cycloolefin (co)polymers possessing excellent characters concerning their optical property, high transparency, heat resistance, and oil absorbency, from an inexpensive raw material of crude DCPD in a stable, continuous, and long-standing process. In the continuous preparation of tetracyclododecenes described in the present invention, it is possible to produce the targeted product in high efficiencies in the effective utilization of the raw materials exemplified by the separation and recovery of 2-norbornenes after the reaction. It is also possible to maintain a stable, continuous, and longstanding operation based on the suppression of ill effects deriving from the accumulation of byproducts such as 2-methyl-2-norbornenes, which easily creep into the circulating 2-norbornenes, by removing at least a part of said products from the reaction system.

2 Claims, 1 Drawing Sheet

PROCESS FOR THE CONTINUOUS PREPARATION OF TETRACYCLODODECENS

FIELD OF THE INVENTION

The present invention relates to a process for a continuous preparation of tetracyclododecenes, more particularly, the invention relates to a process for preparing highly purified tetracyclododecenes (may be abbreviated hereafter as TCD), which can be a raw material of cycloolefin (co)polymers possessing excellent characters concerning their optical property, high transparency, heat resistance, and oil absorbency, from an inexpensive raw material of crude dicyclopentadiene (DCPD) in a stable, continuous, and longstanding process.

BACKGROUND ART

Cycloolefin (co)polymers are the focus of industrial attention as polymers that possess excellent characters concerning the optical property, high transparency, heat resistance, and oil absorbency. Cycloolefins represented by TCD are a useful raw material for polymer. These cycloolefins are generally prepared using organometallic complex catalysts. A polymerization method is roughly classified into two: one is a single polymerization of cycloolefins polymerized at their olefinic site, or the copolymerization with lower alpha-olefins using Ziegler catalysts or metallocene catalysts. The other is known as the metathesis polymerization that employs the carbene-type catalysts.

With regard to the preparative method of TCD, a typical method is mixing cyclopentadiene (may be called CPD hereafter), dicyclopendtadiene (may be called DCPD hereafter), or a mixture thereof, with norbornene and ethylene, in a heated condition, yielding a reaction mixture containing tetracyclododecenes and norbornenes. This is followed by the recovery and circulation of norbornenes in the reaction mixture. A method of preparing tetracyclododecenes, accompanied with the processes of recovery and circulative re-use of generated norbornenes, is reported, for example, in Japan Open H06-9437. This patent proposes a use of DCPD having the purity higher than a specific value as a raw material, and a circulative re-use of recovered norbornenes generated in the reaction, since the industrially available crude DCPD contains a large amount of impurities. However, the raw material DCPD of high purity mentioned in the above patent is likely to bring about a high cost for the raw material naturally, therefore, rarely adopted in the industrial production.

The present inventors investigated processes that employ crude DCPD as a raw material, and found that a continuous, longstanding operation of producing TCDs involves a possibility of unstable reaction condition due to the impurities present in crude DCPD employed. This leads to inability to continue the operation in an extreme case. The present invention proposes a production method of TCDs using inexpensive crude DCPD as a raw material in a stable, continuous, and longstanding process.

DISCLOSURE OF THE INVENTION

The first item of the present invention relates to a continuous method involving the processes of 1 to 4 that are shown below, for the production of tetracyclododecenes shown by the general formula (3), characterized by inclusion of a process of removing at least a part of 2-methyl-2-norbornenes shown by the general formula (4), which may be contained in the obtained reaction mixture.

1) A process of feeding 2-norbornenes shown by the general formula (1), crude cyclopentadiene and/or dicyclopentadiene, and an olefin shown by the general formula (2) into a reaction vessel continuously for the reaction (where R1 and R2 in these formulae are identical or different functional groups, and are any of a hydrogen atom, a methyl group, or an ethyl group).

General formula (1)

General formula (2)

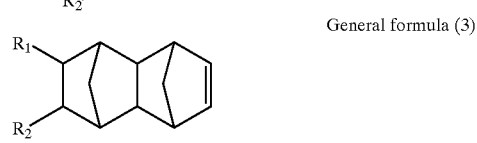

General formula (3)

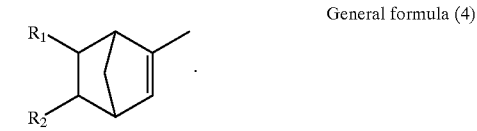

General formula (4)

2) A process of separating 2-norbornenes from the reaction mixture by distillation.

3) A process of circulating at least a part of separated 2-norbornenes to said reaction vessel.

4) A process of separating tetracyclododecenes from the reaction mixture.

The second item of the present invention relates to a continuous production method of tetracyclododecenes shown by the general formula (3) chracterized by inclusion of the following processes of 1 to 7.

1) A process of feeding 2-norbornenes shown by the general formula (1), cyclopentadiene and/or dicyclopentadiene, and an olefin shown by the general formula (2) into a reaction vessel continuously for the reaction (where R1 and R2 in these formulae are identical or different functional groups, and are a hydrogen atom, a methyl group, or an ethyl group).

General formula (1)

General formula (2)

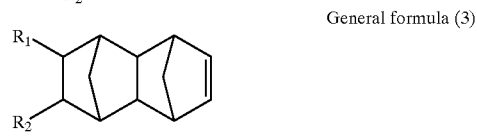

General formula (3)

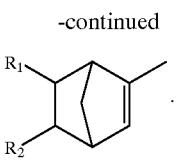

General formula (4)

2) A process of separating an olefin shown by the general formula (2) from the reaction mixture.
3) A process of circulating at least a part of the separated olefin to the above reaction vessel in said process of 2.
4) A process of separating 2-norbornenes from the reaction mixture succeeding said process of 2.
5) A process of circulating at least a part of separated 2-norbornenes to the above reaction vessel in said process of 4.
6) A process of separating and removing 2-methyl-2-norbornenes from the reaction mixture succeeding said process of 4.
7) A process of isolating tetracyclododecenes from the reaction mixture succeeding said process of 6.

According to a method described in the present invention, it is possible to produce TCDs in a stable and longstanding process recovering the generated 2-norbornenes from the reaction mixture, and re-using them in a circulative manner. The detailed description of the invention is given hereafter.

The olefin shown by the general formula (2) in the present invention is precisely taken to mean ethylene, propylene, 1-butene, trans-2-butene, and is-2-butene.

The 2-norbornenes (may be called as alkyl-norbornenes hereafter) shown by the general formula (2) in the present invention are precisely taken to mean 2-norbornene, 5-methyl-2-norbornene (methyl-norbornene), 5-ethyl-2-norbornene (ethyl-norbornene), and 5,6-dimethyl-2-norbornene (dimethylnorbornene). The endo form and the exo form of these compounds may be included in this category if they exist.

The tetracyclododecenes shown by the general formula (3) are precisely taken to mean tetracyclododecene (1,4:5,8-dimethano-1,2,3,4,4a,5,8,8a-octahydronaphthalene), methyltetracyclododecene(2-methyl-1,4:5,8-dimethano-1,2,3, 4,4a,5,8,8a-octahydro-naphthalene), ethyltetracyclododecene((2-ethyl-1,4:5,8-dimethano-1,2,3, 4,4a,5,8,8a-octahydronaphthalene),and dimethyl-tetracyclododecene(2,3-dimethyl-1,4:5,8-dimethano-1,2,3, 4,4a,5,8,8a-octahydronaphthalene). The steric isomers of these compounds such as the endo-exo form, the endo-endo form, the exo-endo form, as well as the steric isomers substituted with different groups may be included.

FIG. 1 illustrates a process flow exhibiting a preferred embodiment of the present invention. In the figure, the feed line of norbornenes necessary at the initiation of the reaction is omitted, and Number 1 means a solvent vessel. It is preferred to employ a solvent having the boiling point of 50–180 degrees centigrade under the ordinary pressure in a preferred embodiment of the invention. The purpose of using solvents lies in the decrease in the concentration of each component in the reaction system leading to reduced generation of heavy-end, which is a byproduct, and especially in the prevention of solidification of the circulating 2-norbornenes when they are employed in the reaction system. It is preferred that the boiling point of the employed solvent is close to that of 2-norbornenes. In more detail, aromatic and aliphatic hydrocarbons having a carbon number of 6 to 8 are preferred.

The hydrocarbon solvent is precisely taken to mean benzene, toluene, xylene, cyclohexane, methylcyclohexane, and dimethylcyclohexane. Among them alicyclic or branched aliphatic hydrocarbons are particularly preferred because of their safety to human bodies and the environment. They include preferably, for example, iso-hexane, iso-heptane, iso-octane, cyclohexane, methylcyclohexane, dimethylcyclohexane, and ethylcyclopentane. Here the compounds like iso-hexane, iso-heptane, and iso-octane are taken to mean hexane, heptane, and octane that possess a hydrocarbon branch or branches larger than or equal to the methyl group. They may be employed regardless of the substituted position or their isomeric form. The preferred examples include 2-methylpentane, 3-methylpentane, 2,3-dimethylbutane, 2-methylhexane, 3-methylhexane, 2,3-dimethylpentane, 2,4-dimethylpentane, 2,2,3-trimethylbutane, 2-methylheptane, 3-methylheptane, 4-methylheptane, 2,3-dimethylhexane, 2,4-dimethylhexane, 2,5-dimethylhexane, 2,2,3-trimethylpentane, 2,2,4-trimethylpentane, 2,3,4-trimethylpentane, and 2,3,3-trimethylpentane. They may be employed regardless of the relative position of substitution for any two methyl-groups.

In a process employing a solvent and intended to recover 2-norbornenes together with the solvent, it is possible to use water for cooling the distillation condenser (not shown in FIG. 1). Water or seawater may be used. The temperature of the cooling medium is generally set to 0–95 degrees centigrade depending on the species and the amount of the solvent. Since the boiling point of 2-norbornenes is 95 degrees, loss of 2-norbornenes into the exhaust gas is possible depending on the distillation pressure. From this viewpoint, the distillation pressure at the top of a distillation tower is preferably set to 10–200 KPa, more preferably to 10–100 KPa, while the preferred temperature of the cooling medium is 0–80 degrees, although it depends on the species and the amount of used solvent. Note that a solvent lost in the exhaust gas at the time of distillation may be substituted in the solvent vessel with a supplement in a proper amount.

Alkylnorbornenes, which are heavier than 2-norbornenes, are still liquid at room temperature, therefore, not needed to employ a solvent for preventing solidification of the reaction system. In such cases addition of solvent is not required in the process flow, as is necessary for 2-norbornenes. Naturally it is still possible to employ a solvent in these occasions. The preferred solvent is one that can be recovered together with the component intended for the circulative re-use in the process, preferably of 2-norbornenes or an olefin, more preferably 2-norbomenes. For this reason preferred are solvents having boiling points close to 2-norbornenes, usually solvents having the identical carbon number to 2-norbornenes.

Number 2 in FIG. 1 means a vessel for crude dicyclopentadiene. Under a usual reaction condition described in the present invention, DCPD decomposes to CPD. Crude DCPD is Industrially obtained with ease. Therefore, crude DCPD may be used in place of CPD as is explained below. It is desirable to use crude dicyclopentadiene as a raw material for the reactions described in the present invention, as crude dicyclopentadiene is inexpensive and may be obtained industrially in a large quantity. It comes from the residue oil recovered at the heat decomposition or the contact decomposition of light hydrocarbons like naphtha for producing lower olefins like ethylene. As it is available as a byproduct, it contains a large number of impurity components as mentioned in the above patent. It is usually refined by distillation, and contains hydrocarbons having the same carbon number as or close to DCPD (10). This leads to a high cost of refined DCPD of high purity inevitably. The present invention is characterized by the use of inexpensive crude DCPD as a raw material, which may be accepted if the purity of DCPD is higher than 70% by weight. Use of DCPD with the purity lower than that value will bring about a very low production efficiency in the TCD production, and would be non-economical. As is explained below, CPD may also become a raw material, and crude DCPD gives no harm when it contains CPD. Therefore, the above purity is concluded to relate to the content of both DCPD and CPD in a mixture.

In a method described in the present invention, crude CPD may be used as a raw material. As explained before, CPD is produced usually by the heat decomposition of DCPD. In that case, many of impurities existent in crude DCPD are similarly decomposed by heat to yield hydrocarbons, which are identical or close to CPD in the carbon number. Therefore, products of DCPD decomposed by heat may be simply called as the crude CPD, which contains many impurities similar to the crude DCPD. It is preferred that the crude CPD employed in the present invention has the purity higher than 70% by weight similar to the crude DCPD.

Number 3 in FIG. 1 points a vessel for an olefin. More precisely, it is for storing ethylene, propylene, 1-butene, trans-2-butene, or cis-2-butene. The molar ratio of employed olefin to dicyclopentadiene (converting 2 moles of cyclopentadiene to one mole of dicyclopentadiene) is 0.5–50, preferably 1–40, more preferably 1.2–30. At a condition having the above ratio in less than 0.5, norbornenes are generated in an amount smaller than the norbornenes consumed during the production period of tetracyclododecenes, making it difficult to circulate a stationary amount in the reaction system. Addition of an olefin in large excess is also not preferred as a large amount of energies are consumed in recovering the olefin.

It is possible to synthesize 2-norbornenes by the reaction of cyclopentadiene and/or dicyclopentadiene with an olefin regardless of its carbon number in a condition involving the reaction temperature in 100–350 degrees centigrade and the reaction pressure in 0.1–40 MPa. In a production process described in the present invention, norbornenes are simultaneously produced with tetracyclododecenes in a condition set for the latter under the co-existence of an olefin and dicyclopentadiene and/or cyclopentadiene. As is described in the later section, at least a part of 2-norbornenes are recovered, and circulated to the reaction process for the re-use.

In the process flow, dicyclopentadiene and/or cyclopentadiene are introduced into the reactor 5 by the transfer pump 4. An olefin is first pressured by a pressuring pump (not shown in the flow), and introduced into the reactor 5. The molar feed ratio of norbornenes to dicyclopentadiene is 1–20, preferably 1.5–15, more preferably 2–10. Here the molar amount of supplied cyclopentadiene and/or dicyclopentadiene is calculated based on the molar amount of dicyclopentadiene (for example, 2 moles of cyclopentadiene are equivalent to 1 mole of dicyclopentadiene).

When norbornenes are employed for the reaction in a large amount, the yield of heavy products becomes comparatively small. But the amount of circulation becomes large, and requires a large amount of energies at distillation, and thus it is not advantageous. When dicyclopentadiene and/or cyclopentadiene are employed in a large amount, the reaction yields heavy products in large quantity, resulting in the decreased efficiency for the raw materials.

The production reaction of tetracyclododecenes is carried out in the reactor 5 employing the above compounds as the raw material. Any of the complete mixing type or the piston flow type can be employed for the reactor 5. As the commercial product of the piston type reactor, there are Static Mixer made by Noritake Company, Thruzer Mixer made by Sumitomo Heavy Machines, and Sukeya Mixer made by Sakura Industry. The reactor 5 accommodates to the single step type or the multi-step type of more than 2 steps. The complete mixing type reactor and the piston type flow reactor may be employed in parallel or in series.

The LHSV (liquid hourly space velocity) in the reactor 5 is set to 0.5–10, preferably 0.7–8, more preferably 1–6. With the LHSV larger than 10, the reaction yields a large amount of unheated components, which prevents the effective production. With the LHSV smaller than 0.5, the reaction produces a large amount of heavy products leading to a decreased efficiency for the raw materials, and decrease in the productivity per hour.

The pressure necessary for the reaction is 1–50 MPa, preferably 2–40 MPa, and more preferably 3–10 MPa. The favorable reaction temperature is 170–280 degrees centigrade, preferably 180–270 degrees, and more preferably 200–260 degrees. In a condition using dicyclopentadiene as a raw material, the reaction at above 100 degrees causes facile decomposition of dicyclopentadiene to cyclopentadiene, and thus is favorable.

In a method according to the present invention, it is preferred that an olefin having relatively low boiling point is dissolved sufficiently in the liquid phase containing norbornenes, cyclopentadiene and/or dicyclopentadiene. When a solvent is employed in the reaction system, it is preferred that the olefin is dissolved in the solvent sufficiently. The dissolved state of an olefin depends on the molar mixing ratio of norbornenes, dicyclopentadiene and/or cyclopentadiene, and an olefin. For example, at a ratio of norbornene/dicyclopentadiene/ethylene=8/1/1 with the reaction temperature of 180 degrees and without the presence of a solvent, pressures of more than 2.5 MPa are necessary for the dissolution of ethylene. In case of higher ethylene contents and higher temperatures, higher pressures are needed. For example, the reaction at 260 degrees requires roughly a pressure of more than 3.9 MPa.

When a solvent is employed, it facilitates the reaction at low pressures since the dissolution of an olefin becomes feasible at lower pressures. At any rate, selection of an adequate reaction condition is necessary for obtaining tetracyclododecenes in high yields so that the reaction proceeds in the liquid phase, and the gas phase does not exist substantially within the reactor.

In a reaction according to the present invention, specific byproducts 2-methyl-2-norbornenes shown by the general formula (4) are by-produced as a result of employing crude DCPD, crude CPD, or a mixture thereof as a raw material. They have structures similar to the targeted norbornenes as well as the adjacent carbon number.

In case of using ethylene as the olefin, for example, 2-norbornenes are the targeted products, and 2-methyl-2-norbornenes are the main byproduct. There is only a difference of one carbon between the main product and the byproduct. Therefore, it is quite probable that the byproduct 2-methyl-2-norbornenes may contaminate the norbornenes obtained in the recovery by distillation. When the recovered norbornenes are circulated to the reactor 5, the by-produced 2-methyl-2-norbornenes may be circulated in the reaction system in accompany.

In a reaction condition described in the present invention, however, it became clear that 2-methyl-2-norbornenes do not react actively, and keep circulating in the reaction system unchanged. Therefore they are discharged from the reactor 5 almost unchanged. On the other hand, crude DCPD is fed to the reaction system continuously as a raw material. This causes the continuous generation of 2-methyl-2-norbornenes resulting, therefore, in the accumulation of 2-methyl-2-norbornenes in the reaction-circulation system. As they are unsaturated hydrocarbons, it is not that they do not react completely. They do react slightly especially in high concentrations leading to polymerization, etc. For the reason, the accumulation of these compounds is not preferable, since it may result in the termination of process operation in extreme cases.

In the present invention, therefore, a process of discharging at least a part of 2-methyl-2-norbornenes out of the reaction system is to be added, so that the accumulation of them in the reactor 5 is prevented. In more detail, it is necessary to execute a removing operation of 2-methyl-2-norbornenes in the processes succeeding the reaction, so that the discharged amount from the reactor 5 per unit time becomes equal to or larger than the introduced amount of 2-methyl-2-norbornenes per unit time.

Since the boiling points of 2-methyl-2-norbornenes are close to those of 2-norbornenes, this removing process is to be executed simultaneously with the discharging process of 2-norbornenes, directly before, or directly after the process. As the boiling points of 2-methyl-2-norbornenes are higher than those of 2-norbornenes, it is preferred to add this process after or simultaneously with the discharging process of 2-norbornenes. In a practical application, a certain content, for example less than 1 wt %, of 2-methyl-2-norbornenes to 2-norbornenes existent in the circulating flow does not affect the continuous operation. Therefore, handling of conditions in the distillation process or other processes may suffice to suppress the ratio of 2-methyl-2-norbornenes to 2-norbornenes in the circulating flow below 1 wt %. When the reaction system involves multiple reaction flows, the limiting concentration is set against the total of flows. In a practical operation for a continuous process, the content became constant at a value less than 1 wt %. The above operation of suppressing the concentration of 2-methyl-2-norbornenes within 1 wt % against the norbornenes in the circulating flow may also be determined by proper changes in the ratios of fed raw materials including the crude DCPD, the reaction temperature, and the distillation condition. When propylene or 1-butene is used as an olefin shown by the general formula (2), 2-methyl-2-norbornenes defined by the general formula (4) are taken to mean 2,5-dimethyl-2-norbornene, 2,6-dimethyl-2-norbornene, 5-ethyl-2-methyl-2-norbornene, and 6-ethyl-2-methyl-2-norbornene.

The detailed description of the processes is given hereafter starting from the distillation process that follows the reaction. As is shown in FIG. 1, the reaction mixture discharged out of the reactor 5 is introduced into the first distillation tower 6, and adjusted to a pressure of 0.1–1 MPa. Here mainly the unreacted olefin is separated from the top of the tower. The distillation condition is set to a pressure within 100–1000 KPa and a temperature of 25–45 degrees at the top and a pressure within 100–1000 KPa and a temperature of 25–100 degrees at the bottom freely. Pressurization at a little higher than the ordinary pressure facilitates the condensation of the top gas by inexpensive seawater or the industrial water.

The olefin separated by said process may be circulated again to the reactor 5. Any method may be employed for the circulation of an olefin into the reaction system. They may be sent back to the olefin vessel, or introduced to the reactor 5 indirectly through the line 10 using a pressurization pump (not shown in the process flow) on necessity. The circulative re-use of an olefin combined with the recovery process helps to increase the reaction yield per olefin.

In a reaction condition according the present invention, the reaction mixture contains the unreacted cyclopentadiene, when it is employed as a raw material, as well as the cyclopentadiene produced by the decomposition of dicyclopentadiene. Cyclopentadiene is usable again as a reacting raw material. It may easily creep into the olefin fraction obtained after the distillation since its boiling point is close to those of olefins. For the reason, the re-use of an olefin as a raw material through the separation and recollection corresponds at the same time to the re-use of accompanying cyclopentadiene as a raw material, and is quite welcome. Especially in case of using butenes as an olefin, this effect is considerable. In case of treating an olefin to depressurized separation as is in the preceding example, products of low boiling points such as cyclopentadiene are easily lost during the process, and thus the method is not preferred.

In the process flow, the reaction mixture removed of an olefin is discharged from the bottom of the first distillation tower 6, and led into the second distillation tower 7. From the top of the second distillation tower 7, norbornenes, or norbornenes containing a solvent when the solvent is used in the reaction, are separated and recovered. This fraction is circulated to the reactor 5 for the re-use via the line 11. Here the distillation condition is set up so that the reaction mixture discharged from the bottom of the second distillation tower 7 contains 2-methyl-2-norbornenes shown by the general formula (4). These compounds are difficult to react as is shown in the previous discussion, and also are difficult to decompose.

The distillation condition for the second distillation tower 7 is set to 0.1–200 KPa at the top, preferably 1–100 KPa under a temperature of 35–96 degrees centigrade, and 0.1–200 KPa at the bottom, preferably 1–100 KPa under a temperature of 40–190 degrees. The distillation towers are filled up with various fillers in order to raise the distillation efficiency and equipped with the refluxing device. The number of theoretical plates in each distillation tower is set to 1–100 plates, preferably 2–50 plates, and more preferably 3–30 plates. The reflux ratio is determined according to the separation status of each tower, but a value of 1–50 is appropriate.

Norbornenes, or mixtures of norbornenes and a solvent in case of using the solvent in the reaction, are discharged from the top of the second distillation tower 7. The discharged norbornenes, or the mixtures of norbornenes and a solvent in case of using the solvent in the reaction, are circulated to the reactor 5 for the re-use as a raw material via the line 11. The circulated norbornenes (may be called as the circulating norbornenes hereafter) are mixed either with the solvent supplied from the solvent vessel 1, or dicyclopentadiene supplied from the dicyclopentadiene vessel 2, and conveyed to the reactor 5 by the liquid transfer pump 4.

It is probable that compounds of low boiling points such as the remaining cyclopentadiene, which can not be completely separated from the reaction mixture at the first distillation tower 6, may creep into the circulating norbornenes. Therefore, the re-sue of them as a raw material improves the yield of product per cyclopentadiene or dicyclopentadiene, and thus is preferred.

It is possible to produce highly purified norbornenes by dividing a part or all of the circulating norbornenes into the purified norbornene and the circulating norbornene by distillation. It is also possible to produce highly purified norbornenes by dividing the circulating norbornenes into three flows, that is, 1) Component such as cyclopentadiene having low boiling point, 2) Highly purified norbornenes, and 3) Circulating norbornenes (distillation tower for each is not illustrated in the process flow). In this case, the separated cyclopentadiene in the first component may preferably be re-used by re-mixing with the circulating norbornenes.

In the process flow shown in FIG. 1, most of 2-methyl-2-norbornenes shown by the general formula (4) are discharged from the bottom of the second distillation tower 7. In addition, a part of 2-methyl-2-norbornenes shown by the general formula (4) may be discharged from a distillation tower (not illustrated) in the above methods of dividing the circulating norbornenes into two or three flows including a flow of purified norbornenes by distillation. As is stated before, the core of this consideration lies in the prevention of 2-methyl-2-norbornenes creeping into the circulating flow that enters the reactor 5 as much as possible.

The reaction mixture extracted of norbornenes is discharged from the bottom of the second distillation tower 7, and sent to the third distillation tower 8. The bottom flow contains a large portion of the previously mentioned 2-methyl-2-norbornenes, while the top flow does not. In more detail, the operation condition of the second distillation tower 7 must be set up so as to prevent the contamination of the 2-methyl-2-norbornenes in the circulating flow entering the reactor 5. It is repeatedly stressed that the amount of 2-methyl-2-norbornenes per unit time coming out of the reactor 5 must be controlled so as to level off or exceed the amount of 2-methyl-2-norbornenes per unit time entering the reactor 5. This is achieved by optimizing the operation condition for the second distillation tower 7 in the processes following the reaction.

The unreacted dicyclopentadiene is separated from the top of the third distillation tower 8. The pressure at the position is preferably less than 50 KPa. The separated dicyclopentadiene may be re-used as a raw material. In the process shown in FIG. 1, 2-methyl-2-norbornenes are extracted from the top of the third distillation tower 8-together with DCPD or the like, and at least a part of 2-methyl-2-norbornes is disposed out of the system.

The reaction mixture removed of the unreacted dicyclopentadiene is discharged from the bottom of the third distillation tower 8, and sent to the fourth distillation tower 9. The targeted product tetracyclododecenes are extracted from the top of the fourth distillation tower 9, and the heavy end containing the heavier compounds than tetracyclododecenes is discharged from the bottom. The operation condition of the fourth distillation tower 9 is set preferably to a pressure of less than 30 KPa and a temperature of less than 200 degrees centigrade.

Addition of appropriate oxidation inhibitors or polymerization inhibitors to the raw material is allowed in this reaction. Preferably added are phenolic compounds such as hydroquinone, 2,6-di-t-butylphenol, 2,6-di-t-butylcresol, 4-methoxyphenol, and hydroxylamines such as N, N-dimethylhydroxylamine or N, N-diethylhydroxylamine. The necessary amount of them against the total raw material fed into the reactor is usually 10–10,000 ppm(wt), preferably 50–5,000 ppm(wt). Addition to the product tetracyclododecenes is also allowable.

Figure 1:
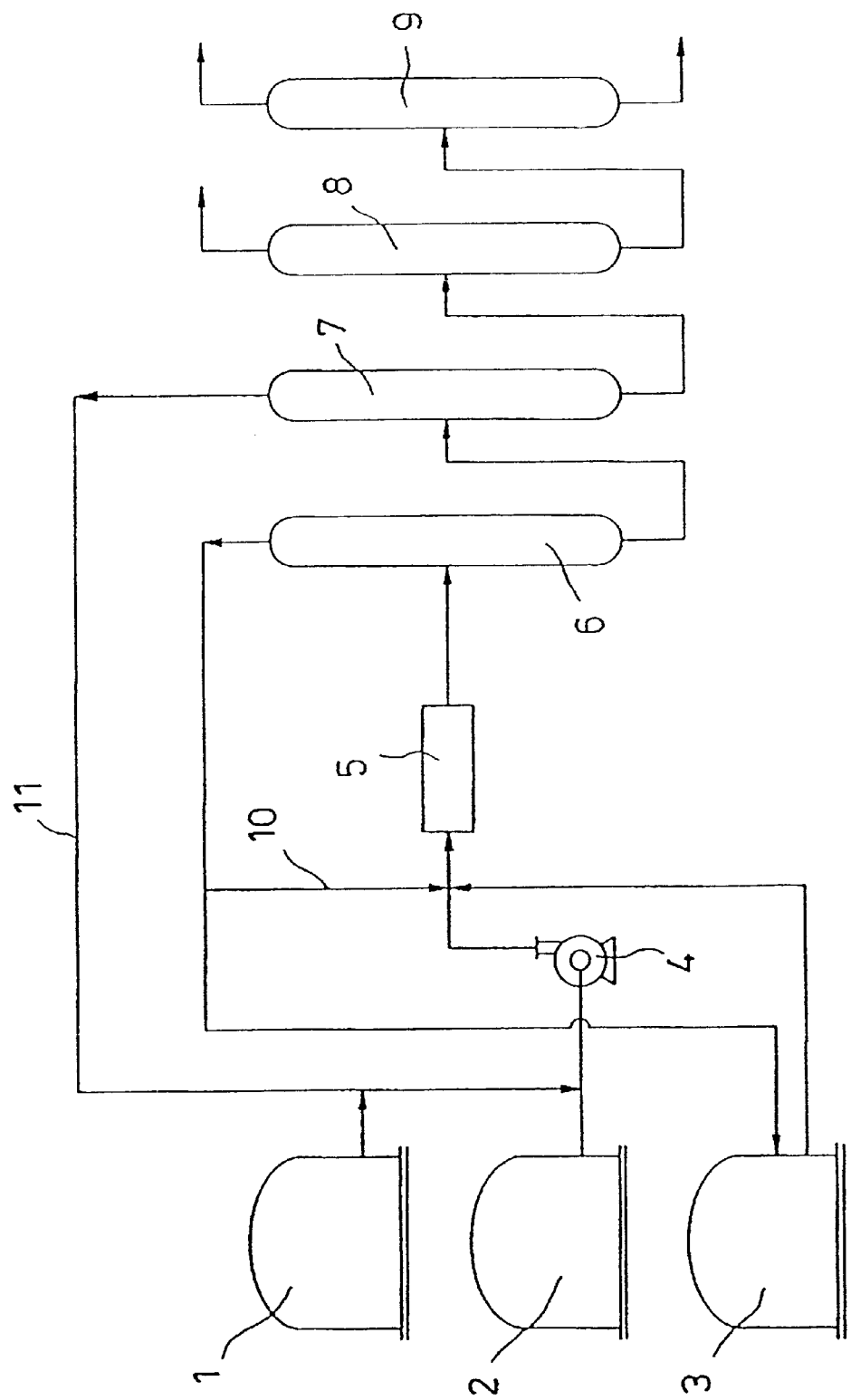
FIG. 1 illustrates a process flow for a preferred embodiment of the present invention. In the figure, 1 denotes the vessel for solvent, 2 the vessel for dicyclopentadiene, 3 the vessel for an olefin, 4 the transfer pump, 5 the reactor, 6 the first distillation tower, 7 the second distillation tower, 8 the third distillation tower, and 9 the fourth distillation tower.

Numbers 10 and 11 are the lines for recovering and circulating an olefin or 2-norbornenes respectively.

BEST MODE FOR CARRYING OUT THE INVENTION

While the invention will be described in detail and with reference to specific examples and comparative examples hereafter, it will be apparent to one skilled in the art that the present invention is not limited in any manner by examples thereof unless they deviate from the purport of the invention.

EXAMPLE 1

A continuous preparation of tetracyclododecenes was carried out employing the equipment in FIG. 1. A mixed raw material comprising 2-norbornenes/ethylcyclopentane (solvent) mixed in a ratio (wt) of 85/15 was introduced into the reactor 5, reacted with commercially available dicyclopentadiene and ethylene. These materials were continuously fed from the vessels 1, 2, and 3 respectively during the reaction at a molar ratio of norbornenes/dicyclopentadienelethylene=5/1/1.7. The purity of the initially fed norbornenes was 99.7 wt %. The purity of the commercially available crude dicyclopentadiene and ethylene, which were continuously fed into the reactor, was 94.7 wt % and 99.9 wt % respectively. The continuous operation of the reaction was set up at the LHSV of 2h-1 and the temperature of the reactor 5 in 230 degrees and the pressure of 5 MPa. After the reaction, the reaction mixture was transferred to the first distillation tower 6. It was treated for continuous distillation at the tower 6 having theoretical plates of 20 under a pressure of 400 KPa. Ethylene was separated continuously from the top of the tower, pressurized by the pump (not shown in the figure), and sent back to the reactor 5 via the line 10 for the circulative use.

The reaction mixture discharged from the bottom of the first distillation tower 6 was sent to the second distillation tower 7 having theoretical plates of 10 for the distillation under a condition comprising the pressure in 20 KPa and the temperature at the top of the tower in 35–43 degrees. A mixture of norbornenes and ethylcyclopentane was obtained from the top of the tower. From 1 hour onward after the start of the continuous reaction, the reaction mixture contained 2-methyl-2-norbornenes in 0.36 wt % against the contained norbornenes. This figure did not change substantially during the longstanding operation of this continuous operation.

The recovered liquid substance extracted from the top of the second distillation tower 7 was mixed with the raw material dicyclopentadiene via the line 11, and fed continuously into the reactor 5 with the help of the liquid transfer pump 4 for the re-use. The distillation condition of the second distillation tower 7 was set up so that the discharged product from the bottom contained 2-methyl-2-norbornenes in the amount of which corresponds to 20 wt % of those produced by the reaction. The reaction mixture coming out of the bottom of the second distillation tower 7 is sent to the third distillation tower 8, extracted of dicyclopentadiene from its top. The reaction mixture was discharged from its bottom and sent to the fourth distillation tower 9.

The product tetracyclododecenes were obtained from the top of the fourth distillation tower 9 with the purity of 97.0 wt %. All these operations were conducted continuously in a stable condition for more than 250 days without exhibiting any periodical changes. The conversion of dicyclopentadiene was 92%, and the yield of tetracyclododecenes having the purity of 97.0 wt % was 75% (based on the fed dicyclopentadiene).

Comparative Example 1

The continuous reaction in EXAMPLE 1 was repeated except that the product coming out of the bottom of the second distillation tower 7 was controlled so that it did not contain 2-methyl-2-norbornenes. To be precise, the distillation condition of the second distillation tower 7 was set up so that the most part of 2-methyl-2-norbornenes generated in the reactor 5 crept into the fraction of 2-norbornenes, which was extracted from the top of the second distillation tower 7. Then the fraction was sent back to the reactor 5 as the circulating norbornenes. As the result, the content of 2-methyl-2-norbornenes in the circulating norbornenes was shown to increase gradually but obviously from 0.36 wt % at 1 hour after the start of the continuous reaction to 5 wt % after 1 day. As the increase was noted to proceed still, the operation was stopped at this point.

Industrial Applicability

In the continuous preparation of tetracyclododecenes described in the present invention, it is possible to produce the targeted product in high efficiencies in the effective utilization of the raw materials exemplified by the separation and recovery of 2-norbornenes after the reaction. It is also possible to maintain a stable, continuous, and longstanding operation based on the suppression of ill effects deriving from the accumulation of byproducts such as 2-methyl-2-norbornenes, which easily creep into the circulating 2-norbornenes, by removing at least a part of said byproducts from the reaction system. For these reasons the industrial utility value of the present invention is quite significant.

What is claimed is:

1. A method of preparing continuously tetracyclododecenes shown by a below described general formula (3), characterized by inclusion of the following processes of steps 1 to 4, and by inclusion of a process of removing from a reaction system at least a part of 2-methyl-2-norbornenes shown by a below described general formula (4), which are contained in a reaction mixture; said steps 1 to 4 including:

1) feeding 2-norbornenes shown by a below described general formula (1), crude cyclopentadiene and/or dicyclopentadiene, and an olefin shown by a below described general formula (2) continuously into a reactor for a reaction (where R1 and R2 in these formulae are identical or different functional groups, and are any of a hydrogen atom, a methyl group, or an ethyl group), and wherein

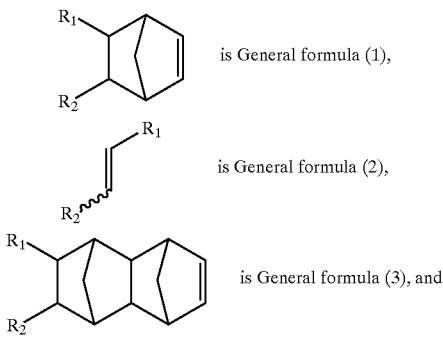

is General formula (1), is General formula (2), is General formula (3), and

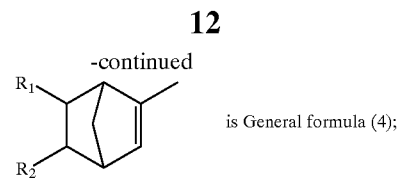

is General formula (4);

2) separating 2-norbornenes from the reaction mixture by distillation;
   3) circulating at least a part of separated 2-norbornenes to the reactor;
   4) isolating tetracyclododecenes from the reaction mixture.

2. A method of preparing continuously tetracyclododecenes shown by a below described general formula (3), characterized by inclusion of the following processes of steps 1 to 7:

1) feeding 2-norbornenes shown by a below described general formula (1), cyclopentadiene and/or dicyclopentadiene, and an olefin shown by a below described general formula (2) continuously into a reactor for a reaction (where R1 and R2 in these formulae are identical or different functional groups, and are any of a hydrogen atom, a methyl group, or an ethyl group); and wherein

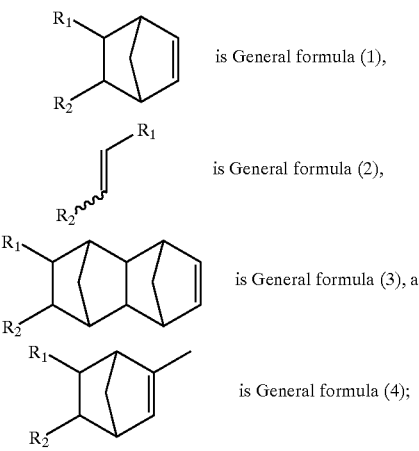

is General formula (1), is General formula (2), is General formula (3), and is General formula (4);

2) separating an olefin shown by the general formula (2) from a reaction mixture;
   3) circulating at least a part of an olefin separated in said process of step 2 to the reactor;
   4) separating 2-norbornenes from the reaction mixture succeeding said process of step 2;
   5) circulating at least a part of 2-norbornenes separated in said process of step 4 to the reactor;
   6) separating and removing 2-methyl-2-norbornenes from the reaction mixture succeeding said process of step 4;
   7) isolating tetracyclododecenes from the reaction mixture succeeding said process of step 6.

* * * * *

UNITED STATES PATENT AND TRADEMARK OFFICE
CERTIFICATE OF CORRECTION

PATENT NO.     : 6,465,703 B1
DATED          : October 15, 2002
INVENTOR(S)    : Fuyuki Aida et al.

It is certified that error appears in the above-identified patent and that said Letters Patent is hereby corrected as shown below:

Column 3,
Line 30, "is-2-butene" should read -- cis-2-butene --;

Column 4,
Line 46, "2-norbomenes." should read -- 2-norbornenes. --;

Column 7,
Line 20, "2-methyl-2-norbomenes" should read -- 2-methyl-2-norbornenes --.

Signed and Sealed this

Sixteenth Day of December, 2003

JAMES E. ROGAN
*Director of the United States Patent and Trademark Office*